Nov. 14, 1939. E. BOURDIEU Plant Pat. 346
PYRACANTHA KOIDZUMII
Filed Oct. 25, 1937
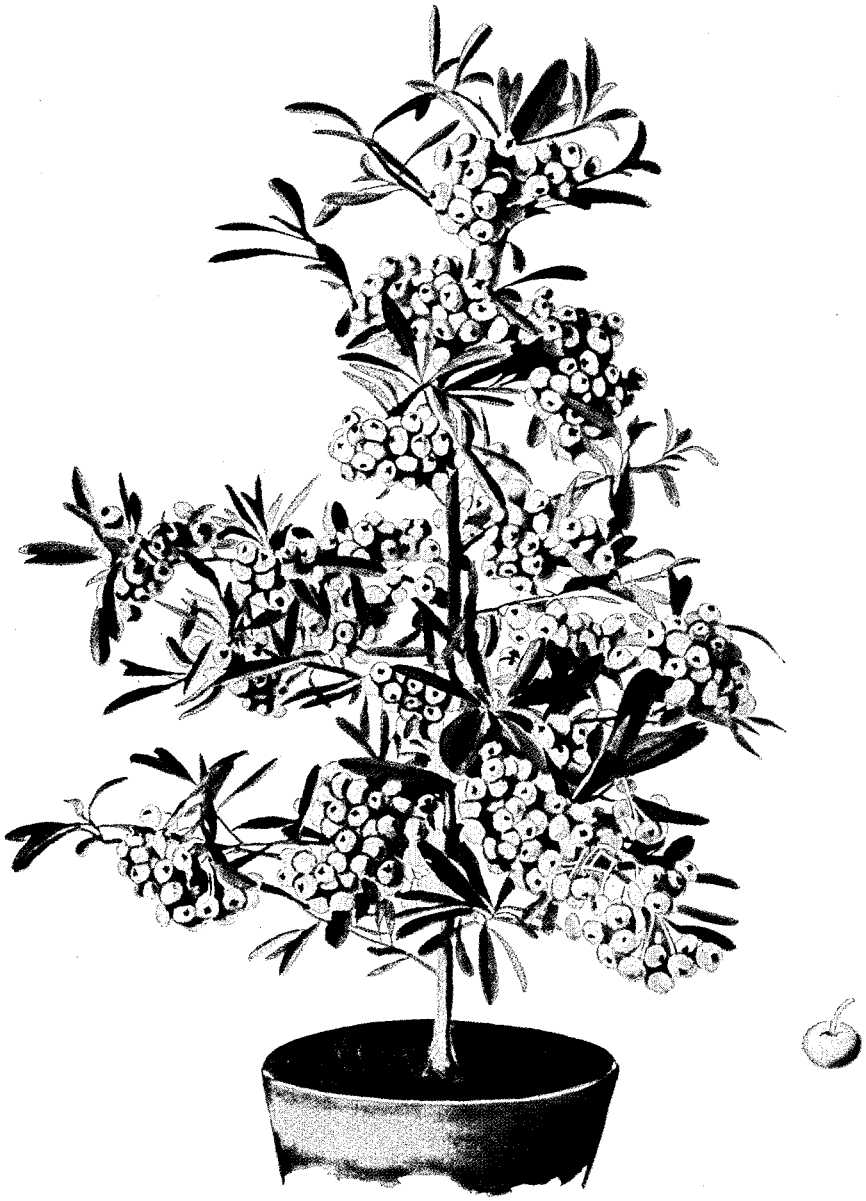
Inventor:
Edmy Bourdieu
By Tefft & Tefft
Attys.

Patented Nov. 14, 1939

UNITED STATES PATENT OFFICE

346

PYRACANTHA KOIDZUMII

Edmy Bourdieu, Ventura, Calif.

Application October 25, 1937, Serial No. 170,806

1 Claim. (Cl. 47—59)

This plant was developed for the particular purpose of providing a potted plant of brilliant appearance, particularly attractive and salable during the winter season.

The drawing is a front perspective view of my plant *Pyracantha koidzumii* and shows a typical specimen as it appears in preferred form as a potted plant.

Parentage:

*Seed parent.*—*Pyracantha koidzumii.*

*Pollen parent.*—Seedling of *Pyracantha koidzumii* x *Pyracantha yunnanensis.*

The original plant was planted in April, 1925, and developed a terminal stock with horizontal laterals which bloomed on the laterals in April 1926. Set green berries in May which turned to red berries in September, 1926, and held them until the following April, 1927, when the plant bloomed again.

I propagated this plant because of its habit of growth, abundance and color of berries and because it retained its size and shape in gallon containers which made it a desirable pot plant.

Another desirable feature was that the birds did not like the berries. I had this plant planted in a group which consisted of five different varieties of cotoneasters and pyracanthas. The birds stripped all of these plants of their berries excepting this pyracantha for which I am applying for a patent.

I then propagated this plant from cuttings in May, 1927; potted the cuttings in two inch pots in September, 1927. I put them in gallon containers in March, 1928, where they developed a central stock with laterals which bloomed in April, 1929; set green berries in May which turned red in September. I have continued this process until the present time with the same results.

The description of the plant (using Ridgway 1912 color standard) follows:

Form:

A vigorous upright growing shrub which has the habit of developing a central stock with alternate horizontal laterals.

Foliage:

Abundance and large in alternate clusters.

*Size.*—1 to 3 inches long; ½ to ¾ inch wide.

Base cunate, tip, classified as emarginate.

*Color.*—New foliage: yellowish oil green, Plate 25, yg–y tone k. Old foliage: yew green, Plate 27'' g–y tone M. Texture: upper side—glossy; under side—smooth. Ribs and veins: mid rib—prominent on under side; veins—light. Edge: smooth. Leaf stem: yellowish oil green, plate 25, yg–y tone g, under side smooth. Stipules—none.

Berries:

*Texture.*—Pithy and dry.

*Size.*—⅜ to ⅝ inch in diameter.

*Stones.*—5, black.

Berries on laterals from main stock, many.

*Form of berries.*—Flat base and short. Color when young, variable shades of green. Color when matured—color for berries in protected or shaded in position, Spectrum red; hue No. 1; tone, full color. Color for berries in exposed position, Scarlet red; hue No. 3; tone, full color. Between vermilion and crimson. Classified as scarlet lake. Position—in sets of three or more.

Thorns:

On main stock, few.

On laterals few, sometimes lacking.

*Color.*—brown.

Flower:

Borne in profusion in terminal clusters on laterals from main stock.

White, 5 petals.

*Petiole.*—Yellowish oil green, Plate 25, yg, tone 1.

*Style.*—Five parts.

*Stamens.*—20.

*Ovary.*—Inferior.

From the foregoing description my plant will be well understood, and I now claim:

The variety of *Pyracantha koidzumii* shown and described, characterized by its ability when grown in pots to develop a central stock with alternate horizontal laterals, an abundance of foliage in alternate clusters on said laterals and an abundance of scarlet red berries in clusters on said laterals, said berries being distasteful to birds.

EDMY BOURDIEU.